US010133048B2

(12) United States Patent
Carloni

(10) Patent No.: US 10,133,048 B2
(45) Date of Patent: Nov. 20, 2018

(54) LASER OPTICAL COUPLING FOR NANOPARTICLES DETECTION

(71) Applicant: NTP NANO TECH PROJECTS S.R.L., Sant'Angelo in Vado (IT)

(72) Inventor: Adolfo Carloni, Pavullo nel Frignano (IT)

(73) Assignee: NTP NANO TECH PROJECTS S.R.L., Sant'Angelo in Vado (IT)

( * ) Notice: Subject to any disclaimer, the term of this patent is extended or adjusted under 35 U.S.C. 154(b) by 56 days.

(21) Appl. No.: 15/324,789

(22) PCT Filed: Jul. 9, 2014

(86) PCT No.: PCT/IT2014/000183
§ 371 (c)(1),
(2) Date: Jan. 9, 2017

(87) PCT Pub. No.: WO2016/006006
PCT Pub. Date: Jan. 14, 2016

(65) Prior Publication Data
US 2017/0205612 A1    Jul. 20, 2017

(51) Int. Cl.
*G01J 1/58*     (2006.01)
*G02B 21/06*   (2006.01)
(Continued)

(52) U.S. Cl.
CPC ......... *G02B 21/06* (2013.01); *G01N 15/1434* (2013.01); *G01N 21/648* (2013.01);
(Continued)

(58) Field of Classification Search
CPC ........... G01N 21/6428; G01N 21/6458; G01N 21/64; G01N 21/6408; G01N 2021/6421
See application file for complete search history.

(56) References Cited

U.S. PATENT DOCUMENTS

2002/0028519 A1*  3/2002  Yguerabide ......... C12Q 1/6816
                                                              436/518
2005/0214789 A1*  9/2005  Moyle ................. B01L 3/50851
                                                              435/6.12
(Continued)

FOREIGN PATENT DOCUMENTS

DE      102007033124 A1    1/2009
WO    WO 2000/63677 A1   10/2000

OTHER PUBLICATIONS

PCT/IT2014/000183 International Search Report dated Mar. 18, 2015.

*Primary Examiner* — David Porta
*Assistant Examiner* — Mamadou Faye
(74) *Attorney, Agent, or Firm* — Arent Fox LLP

(57) ABSTRACT

This patent application pertains to the optical laser microscopy field and proposes a simplified yet specific optical laser coupling method. The proposed method allows for a sensible reduction in size and complexity of laser based microscopes and related applications, especially in the area of nano particles detection and optical biosensing. Particularly the optical laser coupling proposed method can detect optical signals generated from sub-diffractive nanoparticles located in liquid solution on a standard glass coverslip. Thanks to the small size of the required components and to the usage of standard air-lens objective, without the presence of oil or special prism, this method can be easily embedded into a small, lightweight and portable device, which can properly operate even in absence of gravity.

9 Claims, 5 Drawing Sheets

(51) Int. Cl.
  *G02B 21/00*   (2006.01)
  *G01N 21/64*   (2006.01)
  *G02B 21/16*   (2006.01)
  *G02B 21/36*   (2006.01)
  *G02B 27/58*   (2006.01)
  *G01N 15/14*   (2006.01)
  *G02B 21/26*   (2006.01)
  *G02B 21/34*   (2006.01)
  *G01N 21/47*   (2006.01)

(52) U.S. Cl.
  CPC ..... *G01N 21/6458* (2013.01); *G02B 21/0008* (2013.01); *G02B 21/16* (2013.01); *G02B 21/26* (2013.01); *G02B 21/34* (2013.01); *G02B 21/367* (2013.01); *G02B 27/58* (2013.01); *G01N 21/47* (2013.01)

(56) References Cited

U.S. PATENT DOCUMENTS

| | | | |
|---|---|---|---|
| 2008/0068588 A1* | 3/2008 | Hess | G01N 21/6458 356/36 |
| 2008/0095669 A1* | 4/2008 | Kang | G01N 21/6452 422/82.08 |

* cited by examiner

LASER OPTICAL COUPLING FOR NANOPARTICLES DETECTION

CROSS-REFERENCE TO RELATED APPLICATIONS

This application is a National Stage entry of International Application No. PCT/IT2014/000183 filed on Jul. 9, 2014, the entire contents of which is hereby incorporated in its entirety by reference.

TECHNICAL FIELD

The field of technique to which this invention relates is the one of microscopy and in particular of the high-resolution laser microscopy for the optical detection of nanoparticles.

BACKGROUND ART

Scientists in general chemists, physicists, biologists, biotechnologists, pathologists and clinicians in particular, need a microscope to qualitatively observe and quantitatively evaluate natural and material processes at the micro and nanometric scale.

In the area of biosensors for example, particularly in early diagnosis, it is necessary to observe and distinguish the interactions occurring, at nanometric scale, between some molecules of interest and nanoparticles. This brings to relevant results and information gathering according to the particular research in place, therefore allowing for the preventive diagnosis of specific parameters in the field of genomics, proteomics and, in general, of clinical medicine.

A nanoparticle is defined as a small object of spherical form that behaves like a single unit with regard to its transport and properties over time. Particles are generally classified according to their size, in terms of diameter, as "lame particles" from 10.000 to 2.500 nm, "fine particles" from 2.500 to 200 nm and "nanoparticles" from 200 to 1 nm.

Several highly specialized systems have been developed for nanoparticles detection and visualization. Particularly, the electron and the optical microscopy have been proven to be the most reliable techniques, leading to the development of smaller and better instrumentations over time.

Generally, optical microscopy is used for the characterization of organic samples such as cells, bacteria, erythrocytes, etcetera. Electron microscopy is commonly used for the characterization of samples such as inorganic nanoparticles, nanomaterials and single biomolecules, like proteins or DNA.

The boundary between the optical microscopy, limited by the capability to detect nanoparticles up to about 200 nanometers, and the electron microscopy, that can improve this threshold up to a few tenths of nanometers, is mainly represented by the diffraction limit described by Ernst Abbe in 1873.

Abbe's Law states that there is a fundamental limit to the resolution of any optical system and this is dictated by the diffraction of light in a optical medium. Usually, any microscope capable of capturing images with a resolution closer to this theoretical limit is named diffraction limited optical system.

The resolution of an optical microscope is mathematically defined by the Abbe's Law, corresponding to: $d=0.61\ \lambda/NA$, where "d" is the size of the resolved, optically visible, object, "$\lambda$" is the wavelength of the incident light on the object and "NA" is the Numerical Aperture of the lens-objective. Therefore it is possible to obtain higher resolution images either by introducing a light source operating at lower wavelengths or by using a lens-objective having higher NA. Actually, the electron microscope reduces the diffraction limit value by generating beam of electrons, instead of photons, to excite the sample under observation. The wavelength of a beam of electrons is about few tenths of nanometers, so—according to Abbe's Law—it can lower the value of the diffraction limit to about 0.1 nm. Since the resolving power of a microscope is inversely proportional to the wavelength of the incident radiation, by using a beam of electrons it is possible to achieve a resolution better than the one obtained with an optical microscope. Even if the resolution capabilities of electron microscopes are higher than those of optical ones, the latter grant some relevant advantages, particularly in terms of cost reduction for large scale production and applications.

Thanks to the availability of superior lens-objectives and new CCD—Charge Coupled Device—cameras, optical microscopy sometimes can be more cost-effective and simpler than electron microscopy. In the last decade the use of monochromatic sources and the improvements in power and precision of the laser have increased the performances of optical microscopes to a level which is almost comparable with that bigger, more complex and expensive electron microscopes.

By localizing and concentrating a certain amount of energy in a small and well defined area of the sample under observation, the laser optical microscope aims at detecting very small particles, such as single molecules or single nanoparticles, rather than a single chain of DNA or a single protein labeled with nanoparticles. This is possible also thanks to consolidated chemical protocols of pretreatment for labeling, commonly used in many laboratories all around the world.

The possibility of recording the number of individual biomolecular events opens wide opportunities in the field of early diagnosis, aiming at detecting into the sample the presence of DNA or proteins responsible for any pathologies.

Currently, the detection of a certain DNA sequence is carried out by the use of RT PCR—Real Time Polymerase Chain Reaction—combined with molecular biology techniques such as gel electrophoresis. The PCR multiplies a specific sequence of DNA, particularly millions of copies of the same DNA sequence are generated in water solution. This is done in order to amplify, in a purely quantitative and massive manner, the signal of interest. PCR is commonly used because it is able to intercept the need of quantification of a DNA by collecting also an extremely small quantity of the sample. PCR was invented by Kary Mullis in 1993 and was developed to enhance the quantity of a genetic signal. At that time powerful video recording devices, like contemporary ones, weren't available, so there was no chance to look at the single molecule.

Since 1993, the optoelectronic technology sector has made great strides in building different types of laser microscopes able to look at the single molecule.

Any technique for detecting a single molecule involves the physical and dynamic properties of single biomolecules and allows for the indirect measure, through laser microscopes, of the fluorescence properties of chemical molecules used as biomarkers. In this way it is possible to observe biochemical processes which otherwise would not be visible using a common optical microscope. The measurement and the standardization of these processes occur thanks to the acquisition of series of optical and electrical signals from a large and heterogeneous population of biomolecules. A definition regarding the optical detection of a single molecule is given as a process that identifies the characteristics of the sample under observation, allowing to distinguish it by capturing a bright emission signal on a dark-field background with an adequate signal to noise ratio. This has already been well reported in the scientific literature from X. Michalet and S. Weiss in "*Single molecule spectroscopy and microscopy*" *C. R Physique* 3 in 2002 page. 619-644.

The possibility to detect the signal in fluorescence coming from individual molecules and nanoparticles, normally used in diagnostic tests as markers of biomolecules like DNA or proteins, is increased by the right combination between a high-sensitivity device, capable of detecting even single photons, and a low background noise. This statement is reported in the literature by X. Michalet and S. Weiss and A. N. Kapanidis, T. Laurence, F. Pinaud, S. Doose, M. Pflughoefft in "*The power and prospects of fluorescence microscopies and spectroscopies,*" *Annu. Rev. Biophys. Biomol. Struct* 32, 2003, p. 161-182.

Very often it is necessary to rely on laser fluorescence microscopy to discriminate the signal of each individual nanoparticle and this happens not only thanks to the laser power emitted on the sample, but also because of the presence of dichroic filters which are able to chromatically separate the wavelength coming from excited particles from the source emission wavelength. Moreover, for the detection of a single molecule, it is necessary to use a reduced volume of the sample, approximately few femtoliters, in order to limit the Raman scattering coming from the water molecules, which can create a high background noise. This is reported in W. E. Moerner and D. P. Fromm in "*Methods of single molecule fluorescence spectroscopy and microscopy,*" *Rev. Sci Instrum.* 74, 2004, p From 3597 to 3619.

The Confocal Microscopy is based on the use of the laser and it is suitable for studying the interface between a solid surface and air. For this reason, Confocal Microscopy is focused on the visualization of fluorescent molecules deposited on that surface. Confocal Microscopy presents some issues because the laser beam focused by an objective can excessively increase the temperature of the sample thus modifying the experiental conditions.

The Wide-field Microscopy is suitable for studying groups of molecules distributed in the section of a flow channel. However it can neither be used for the distinction of single molecules nor for the detection of nanoparticles with a size smaller than the resolution limit of the instrument. Nevertheless, it represents the basic method to reach at least micrometric vision and becomes an essential component for different kind of laser microscopy techniques which aims at seeing also at nanometric level.

TIRF Microscopy represents the most suitable and modern methodology for biosensing, TIRF Microscopy requires only a small volume of the sample under observation to identity the relevant parameters, since the portion of the total volume under analysis is limited by the penetration depth of the evanescent wave generated by total internal reflection of the laser beam in the slide coverslip. The evanescent wave illuminates both the glass slide and the aqueous solution in contact with it, with a depth of field of 200 nanometers from the glass slide into the aqueous solution. This fact considerably reduces the background noise, allowing the capture of signals from single nanoparticles localized on the surface or close to it. The limited capability of penetration of the evanescent wave in the solution represents an important benefit in biosensors since it drastically reduces the background noise, allowing the detection of nanoparticles on coverslip in real time during experiments and testing of new optical biosensors. In TIRF microscopy the generation of the evanescent wave allows to capture images and record videos of single fluorescent molecules or nanoparticles moving fast and in water solution, floating, and docking with bioreceptors printed on glass coverslip. This technique is used in the field of biosensors for the detection of labelled DNA in solution on the slide coverslip. For example, the availability in industrial scale of DNA microarray, consisting of different sequences of DNA printed on the slide coverslip, coupled with the TIRF microscopy, allows to sense and determine the phases of hybridization between complementary strands of DNA, so it can be discovered the presence or not of a specific sequence of DNA.

Laser Microscopy, thanks to the ability of detecting single molecules, offers many opportunities in the area of biomedical diagnostics, for example in the detection of small strands of DNA or in counting fluorescent nanoparticles used as DNA biomarkers.

At the state of present techniques, a Laser Microscope consists of several essential components such as light sources, mirrors, filters, objective, lenses, a camera and a XYZ manual or automated handling system, arranged all together in order to accurately handle the slide holding the sample.

The optical detection of biomolecules, that generally ranges in size from 5 nanometers, such as single strands of DNA, up to 20 nanometers, such as single proteins, occurs thanks to the attachment with covalent chemical bonds between fluorescent molecules or nanoparticles and the biomolecules of interest, according to predefined chemical protocols.

Commercial samples of spherical nanoparticles, 100 nanometers in diameter, represent an excellent compromise in terms of size either from the chemical standpoint, using them as markers of biomolecules or biomarkers, or from the physical one, since the scattering light allows the user to detect these otherwise invisible nanoparticles.

The labeled biological compound is then placed on the lens-objective of a laser microscope, built according to one of the optical techniques already patented and previously described, and the signal is detected in emission by an infinity optical system generally more or less quite complex, equipped with many components like filters, dichroic mirrors, optical switches and lenses with refined mechanisms made of durable materials like steel or aluminium.

The market availability of standard commercial nanoparticles, with the possibility to purchase any kind of element of the periodic table, delivered in a round spherical shape and characterized from the same diameter size in nanometers, will contribute to the standardization of many biosensing processes.

Nowadays there is a strong pressure towards the development of smaller, more powerful and easier to be used electronic devices. The possibility to optically detect nanoparticles with a simple and original optical method embedded into a small, lightweigth and portable device is a relevant and attractive challenge when compared with the existing expensive, and massive electron microscopes.

The laser optical systems alternative to TIRF microscopy vary depending on the target application. Atomic Force Microscopies are the most used for the study of nanomaterials dispersed into air. Confocal Microscopies are used for the study of fluorescent liquid solutions. TIRF Microscopies are widely used to study interactions between the target sample dispersed in the water layer and the receptor linked to the glass substrate.

The TIRF microscope uses a laser as light source in a total internal reflection configuration. This generates an evanescent wave able to selectively excite the nanoparticles or the single fluorescent molecules dissolved in water solution and located nearby the glass surface. This technology uses the illumination derived from evanescent wave combined with oil immersion objective having, high numerical aperture (NA>1.4) and high magnification (from 60× to 100×). In any TIRF microscope the laser beam is sent to the back focal plane of a lens-objective, out of the optical axis, and the light is focused on the pupil of that lens-objective, giving the instrument the capacity to excite what is located at the surface and to discriminate signal emitted by nanoparticles on a dark-field background. This ensures either a high degree of optical resolution or the ability to maintain the beam in total internal reflection while scanning the slide coverslip. In TIRF Microscopy the process of XY scanning of series of coverslip slides is quite complicated for the interposition of the oil, as optical medium, between the TIRF lens-objective and the slide coverslip. This is mandatory for the light beam in order to provide and maintain the total internal reflection. However, in order to generate an evanescent wave able to illuminate the surface and the nanoparticles, it is not strictly necessary that the beam is totally reflected.

For this reason, it is clear that the possibility of illuminating with a laser beam the slide coverslip, without recourring to the use of a liquid medium for optical coupling like in a oil lens-objective, could represent a unique advantage when providing optical performances slightly lower than those provided by TIRF laser microscopes in exchange of the availability of a much smaller and cheaper laser optical device.

The idea to develop a small efficient video camera for laser microscopy is based on a clever arrangement of the minimum number of required components with the purpose of minimizing size, weight and costs whilst providing adequate optical quality.

Definitely, by using an air-objective and a simple laser based excitation method it would be possible to develop a laser microscope of extremely small size, embedded into a case which is lower than 7 dm3 volume.

Moreover, the possibility of proceeding with the automatic scanning of the slide in the X and Y axis would make this mini laser microscope an optical device with an high potential for telecommunications, research and biomedical imaging.

It's important to notice that in conditions in which the force of gravity is different or even absent, the control of the image of a glass slide should be based on a air lens-objective, since the presence of oil as optical medium is not suggested in these conditions.

The gravity will not affect the liquid solution in which nanoparticles are dispersed, since the volume of the liquid under analysis is extremely small, few picoliters, and is confined in a so thin region of space between a standard microscope slide and the glass slide coverslip, thus minimizing the contribution deriving, from gravitational forces for such small nanometric samples. In optical systems based on air lens-objective, this sandwich of glass slides could be easily inserted in a slide mount in an automatic manner, via, a mechanical arm. This would allow to automate the replacement of the glass slide, accelerating the entire process of analysis for more samples.

In summary, all the already patented optical techniques previously described present optical couplings methods which are substantially different from the one presented in this patent request. Furthermore, these techniques present some critical aspects like complexity, costs, device size, device weight, high sensitivity to minor modifications due to physical misalignments, necessity of a "physical" presence in the laboratory for accurately managing oil between lens-objective and slide coverslip.

Instrumental solutions like TIRF Microscopy therefore require a keen eye combined with multidisciplinary skills of scientific level as they must continuously be subjected to a proper maintenance to provide the best reproducibility of an optical signal. TIRF Microscopy always requires the use of oil as optical medium, either using an immersion oil objective or a prism-objective. These mandatory requirements inherently induce some delays in passing from one sample to another, with the risk to incur into variability and difficulties in maintaining the accuracy of the instrument over time. This makes the whole process of laser scanning more difficult because of variations of the optical coupling between the laser, the oil and the slide coverslip. Therefore, the inner complexity of TIRF Microscopy increases its standard maintenance costs and time spent on instrument's daily maintenance.

In summary, a laser microscope is a complex and sophisticated instrument that requires an high degree of specialization and carefulness either in its design or in its operation. The proposed patent fits within the overall context described.

DISCLOSURE OF INVENTION

It is proposed a method for detecting sub-diffractive nanoparticles in liquid solution (55) on a standard glass coverslip, based on a specific optical coupling (FIG. 1A, FIG. 1B) between a laser diode (60), a lens (70) and the glass coverslip itself (15). The detected image is then captured by a CCD camera (200) through a standard air lens-objective (40).

The optical coupling (FIG. 1B) includes a laser diode (60) with a point of light focused at the rim of a bare slide coverslip (15) with an angle of incidence of 25 degrees, with a tolerance of ±2 degrees for glass and/or plastic substrates, between the laser beam (10) and the plane of the slide coverslip (15). Due to the Snell's Law on refractive indexes, when the laser beam (10) passes through the air-glass interface, it changes its incident angle from 25 to 16 degrees: this is sufficient condition to obtain an internal reflection (45) of the light inside the coverslip. The internal reflection generates an evanescent wave field upon the glass surface with a penetration depth on Z axis.

The proposed optical laser coupling method requires the use of a slide holder (35) sized to accommodate a commercial microscope glass slide (20) of 77×26×1.0 mm size. This glass slide (20) is used as the top part of a linear flow channel and it is drilled in the two ends to achieve an inlet (25) and an outlet (30) for the fluid. The lower part of the flow channel, that's the one closer to the lens-objective (40), is composed of a "bare" slide coverslip (15) of thickness 0.17 mm, possibly with rectangular XY variable size: 24×24 or 24×40 or 24×50 or 24×60 mm. The term "bare" means that the coverslip (15) is a standard and commercially available one, unmodified and untreated, with normal right angle surfaces. The slide coverslip (15) and the glass slide (20) are glued together with a hydrophobic component, like silicon, to delimit a linear flow channel from inlet to outlet. The coverslip does not have any inclined end face like other patents report: US2009/052021A1, (MOGAMI HIDEO [JP] ET AL) 26 Feb. 2009 and EP1281969A2 (FRAUNHOFER GES FORSCHUNG [DE]) 5 Feb. 2003, to avoid the necessity of milling glass on a precise angle. In this way, whilst reducing associated costs, laboratory processes are made simpler, faster and with a low coefficient variation in automatic repeatability.

The penetration depth of the evanescent field for internal reflection systems can be calculated by the formula: $d=\lambda_0/2\pi^*n_1$ of $((\sin^2\theta-(n_2/n_1)^2)^{-1/2}$ where $\lambda_0$, $\theta$, $n_1$ and $n_2$ are, respectively the wavelength of the incident light beam in vacuum, the incidence angle in medium 1 and the refractive indexes in medium 1 and 2. Depending on the refraction index of the liquid solution put on the glass coverslip, for a light beam hitting the glass surface at 16 degrees the penetration depth is calculated in 52 nm for water solution and up to 722 nm for glycerin solution.

Nanoparticles (55) in aqueous solution, that are positioned on the slide coverslip or in proximity to it, may reflect the light in scattering, or absorb it and emit a fluorescence signal, with a signal to noise ratio sufficient to discriminate the nanoparticles (55) from the background noise. The advantage to excite nanoparticles using this simple geometry becomes clear since none of the deeper nanoparticles becomes excited and this eliminates any noisy signals that can arise from a dark field background.

So the detection of nanoparticles (55) occurs scattering or in fluorescence mode and is limited to few hundreds of nanometers on the axis Z. Particularly, the detection of single nanoparticles (55) is optimal on the plane of the slide coverslip (15) and then declines exponentially at few hundreds of nanometers of distance from the slide coverslip (15). So their detection is possible only if the nanoparticles are in contact with the slide coverslip (15) or if they are located in close proximity to it. For these reasons, the vision of nanoparticles on several plans is limited by the penetration depth of the evanescent wave (50). Nevertheless, the nanoparticles that are in motion into the liquid solution can be detected.

The sample under examination can be constituted not only by nanoparticles, but also by human or animal cells, human or animal blood, bacteria, and, more generally, by any other transparent or semi-transparent sample deposited on the slide coverslip (15) that has dimensions ranging between 0.52 mm to 67 nm.

Thanks to the absence of any other physical element but air and glass, this sub-diffractive nanoparticles detection method can properly operate even in absence of gravity.

The proposed method of optical coupling (FIG. 1) greatly simplifies the geometry of optical paths that are arranged in a three dimensional configuration by proposing a finite optical system which, by replacing the CCD camera with a tube lens and extending the system, can become infinite. The proposed optical laser coupling method can be easily integrated into a transportable laser microscope, or optical device, having small size, low weight and self-powering capabilities (FIG. 9).

This optical device (FIG. 9) is presented as a complete video camera system dedicated to micro and nanometric vision of samples, constituted by nanoparticles in solution deposited on a slide coverslip. The optical device (FIG. 9) can be very useful in biomarkers research and in biosensing experiments.

An example of an interaction between biomolecules is the detection of a single strand of DNA in solution using other two single strands of DNA which are complementary to the first one at the two opposite end tails; this method is known, in the biosensors field, as sandwich hybridization method which allows the identification of a specimen responsible of a particular viral infection. In this type of interaction between biomolecules, nanoparticles of 100 nanometers in diameter are ideal markers for the control of hybridization occurring between complementary strands of DNA, thus discerning a positive from a negative value by testing the DNA with, in theory, no need of amplification by PCR. The surface of the nanoparticles, in fact, can be chemically modified and functionalized for the attachment of specific biomolecules such as antibodies or strands of DNA, thus making these biomolecules optically detectable. So it becomes possible to observe in aqueous solution their hybridization to the respective biochemical counterparts covalently bond on the slide coverslip (15), such as antigens or complementary strands of DNA.

The laser optical device (FIG. 9) is able to simultaneously capture optical signals in wide-field transmission microscopy and in internal reflection fluorescence/scattering microscopy. The optical device (FIG. 9) is an alternative and viable solution to the limits that today's laser microscopes available on the market can present in terms of size, volume, weight, complexity and costs.

Particularly, the optical device (FIG. 9) can resolve or distinguish, objects with an optical lateral resolution of 290 nm, other than detecting nanoparticles of smaller size, collecting the optical signals and recording video of the associated gaussian profiles during time. The resolution of the optical device (FIG. 9), calculated on the basis Abbe's Law and considering a blue laser source at 405 nm, can ranges from 810 nanometers for a lens-objective 10× with NA=0.25, to 290 nanometers for a lens-objective 60× with NA=0.85. It is important to notice that a lower Numerical Aperture of the lens-objective value is used due to the air lens-objective (typically, NA<1.0), if compared with the dedicated TIRF oil objective one (typically, NA>1.4). From a technological perspective, an oil based TIRF objective confers a better optical resolution than an air based one, but the presence of oil makes more complicated the management of an automated processes like the XY axis scan rather than the automatic replacement of the glass slide. Moreover, it would be not possible to operate in "oblique" positions or in absence of gravity. The optical device (FIG. 9) has been developed with the purpose to solve these problems too. The field of view of the optical device (FIG. 9) is variable depending on the lens-objective adopted; the field of view has an area XY of 520×400 micrometers for a 10× lens-objective, and is reduced to an area XY of 87×67 micrometers for a 60× lens-objective. The size of the single pixel varies from 400 nanometers, using a 10× objective, up to 67 nanometers using a 60× objective.

The field of view and the pixel size calculated above refers to the acquisition of an image using a CCD camera (200) of 1.3 Megapixel, 1280×1024 pixels, and can vary depending on the dimensions of the type of CCD array and nominal pixel size.

The acquisition of images using the laser, combined with software application for image analysis, confers to the optical device (FIG. 9) the ability to detect nanoparticles (55) of 100 nanometers in size and to discriminate the signal coming from two single nanoparticles of 100 nm size located at a minimum distance of 290 nanometers one each other, which means optical lateral resolution. Anyway, the device performances are still limited by diffraction limit, but this limit can be minimized by using the lower laser wavelength, 405 nm, and the higher numerical aperture NA, 0.85 for a 60× lens-objective. However in the region of dimensions between the optical resolution, 290 nm, and the size of a single pixel of 67 nm, it is not possible to distinguish a clear signal in focus deriving from a single nanoparticle of size included between these two values, but this can be achieved by recording the videos capturing the profile of the gaussian signal on X and Y axis. The monitoring of the Gaussian profile in a database aims at predicting with a certain probability the size, the material and some of physical and chemical properties of the nanoparticles. The monitoring of the Gaussian signal of light emitted by each single nanoparticle allows to detect the position of that nanoparticle on a XY area of the slide coverslip (15) and to quantify in real time the intensity of spots of nanoparticles. Gaussian profiles can be captured and applied on the vision of commercial nanoparticles of 100 nm in size recording videos for tracking their emission signals in liquid solutions.

The optical device (FIG. 9) is able to detect the XY position of a single nanoparticle of 100 nm with a probability which is maximum in correspondence of the brighter pixel, or central pixel, and decreases exponentially in the adjacent pixels, with gray levels, out to the external pixels, black, wherein the output signal is lost.

The color of the laser beam (10) can also be set at different wavelengths such as red at 635 nm or green at 532 nm, depending on the fluorescence of the labels or on the scattering properties of the material under observation or on the necessity, somehow, to have a different wavelength of excitation, e.g. 488 nm, less resolute and compatible with the availability of existing laser diodes.

The optical device (FIG. 9) has a slide holder (35) sized to accommodate a commercial microscope glass slide (20) of 77×26×1.0 mm size, which is used as the upper part of a linear flow channel.

The optical device (FIG. 9) makes use of three optical modalities: wide-filed transmission microscopy, dark-field internal reflection scattering microscopy and dark-field internal reflection fluorescence microscopy. This permits to the end user to optically analyze a surface, avoiding thermal photo damage of the samples and making possible to investigate optically the properties of sub-diffractive nanoparticles on a wide area.

The air lens-objective (40) inserted in the linear motion in Z axis (275) contributes to have a correct focus for the image, in optical transmission, at various heights up to a maximum of some tens of micrometers in function of the working distance of the air lens-objective (40).

The frequency of acquisition of the images for the chase, or the tracking, of the nanoparticles in aqueous solution is a function of the value in fps, frames per second, that CCD camera (200) is capable to capture and this depends on the needs of user; for example for a slow motion image acquisition during time it will be 1 fps, whereas for nanoparticles motion tracking in a certain region of interest should be faster, up to 25 fps.

Transmission imaging is obtained illuminating the slide coverslip (15) with a LED module (FIG. 3) placed perpendicularly above the plane of the coverslip (15) and in line with the optical axis of the air lens objective (40); internal reflection imaging is obtained illuminating the slide coverslip with a laser module (FIG. 2). In both cases, the image is captured using the sensor part of a CCD camera (200) which is placed at 160 mm distance from the back focal plane of the air lens-objective (40).

The optical, device (FIG. 9) is composed of five modules assembled into a single embodiment (FIG. 8) particularly the laser module (FIG. 2), the LED module (FIG. 3), the mechanical module for XY handling (FIG. 4), the microscope module (FIG. 5), and the electronic module (FIG. 7).

The optical device (FIG. 9) is able through automated commands to offer to a user the possibility to perfectly see at micrometer level and to face to nanometric nanoparticles changing between laser sources and choosing the best optical method to detect the sample; in optical transmission microscopy through the illumination with the LED module (FIG. 3); in internal reflection scattering microscopy through the illumination with the laser module (FIG. 2) without use of band pass filter; in internal reflection fluorescence microscopy through the illumination with the laser module (FIG. 3) using a band pass filter centered at the desired wavelength.

A calibration phase of the optical device is required to hit exactly the rim of the coverslip matching the optical coupling (FIG. 1B). This can be accomplished by acting fine adjustments of the mirror (90) and this is possible by acting on the mirror holder (80) and adjusting the position, through an hex key tool, of hex screws passing through service holes (255): this procedure allows a line pointing of the laser beam (10) on the rim of the glass coverslip. Using this fine pointing, it is possible to concentrate the light intensity to the rim, or edge, and obtain a phenomenon of internal reflection (45) of the light able to generate the evanescent wave (50) on the slide coverslip (15) without the use of any optical medium such as oil or prism between the sample and the lens objective.

The laser module (FIG. 2) is fixed on the Y axis linear stage (155) and positioned in parallel with the glass coverslip (15). It is composed of a laser diode (60) operating as light source in the visible range, generally blue, green or red, equipped with a thermoelectric cooler (65). The laser diode (60) emits a laser beam (10) on a lens (70) and is directed towards a first mirror (85) attached to a holder (75), and then towards a second mirror (90) attached to another holder (80). All of these components are closed internally to an Alcoa aluminium box (115), to avoid undesired stray light. On the upper side of the aluminum box (115) there is a slot (95) which allows the laser beam (10) to exit with the desired angle of 25 degrees. The upper side of the aluminum box (115) has also an extension on one to accommodate a first block of movement (140, 150, 165). The laser beam (10) is focused, through the plane-convex lens (70) having a focal length of 150 mm, in order to hit the rim of the slide coverslip (15), causing a linear reflection of the light into its overall length. Switch on/off and regulation of light intensity of the laser diode (60) is done through electrical signals and cables connected to the electronic board of the laser (225), which is attached to the first electronic board (215). These commands are controllable by an external touch screen interface (270).

The LED module (FIG. 3) is placed perpendicular to the slide coverslip (15), on the same axis of the air lens-objective (40) hut at its opposite side. It is composed of one chip LED (100), one iris (105), one condenser lens (110), one square mirror (125) and one photodiode (135), all of them enclosed into a suitable container (129). The RGB multicolor chip LED (100) is equipped with three LED operating at different wavelengths: blue at 460 nm, green at 530 nm and red at 630 nm. In front of the LED is placed the iris (105) and then the condenser lens (110), to project the LED light perpendicular to the slide coverslip (15), at the height of the glass coverslip (15), in correspondence of the optical axis of the air lens-objective (40). The iris (105) has a lateral bay to accommodate a square mirror (125) adapted to deflect an infrared signal coming from outside of the optical device (FIG. 9). This signal comes from a remote control and is directed to a photodiode IR receiver (135)

located inside the LED module (FIG. 3). The choice of the emission color of the LED module (FIG. 3) is controlled by an external remote control.

Switch on/off and the regulation of light intensity of the LED (100) are driven by electrical signals through cables connected to the first electronic board (215). The relative commands are sent by the touch screen interface (270). Thanks to the LED module (FIG. 3) the optical device (FIG. 9) can also operate in optical transmission, because it can illuminate the slide coverslip (15) at three different wavelengths: red, green or blue. The lens-objective then captures images in transmission or absorption. The imaging in the wide field transmission microscopy is used in the detection of nanoparticles (55), as it allows a first rapid method to reach the focus in microscopy on the surface of the slide coverslip (15).

The mechanical module for XY handling (FIG. 4) is located on the external side of the aluminium box (115). It is composed of two blocks of movement for XY axis and of a glass slide holder (35), connected through an aluminum support to the X axis linear stage (150).

The first block of movement for X axis (140, 150, 165) is composed of one X axis linear stage (150) coupled, through two gears (165) having ratio 1:1, with one DC motor (140). The two wears (165) are respectively inserted: one, by means of axle box, into the rotational axis of the handler of the X axis linear stage (150), and the other one into the rotational axis of the DC motor (140). This allows for the inversion at 90 degrees of the rotational axis of the handler, thus realizing the first block of movement (140, 150, 165). The X axis linear stage (150) and the geared DC motor (140) are locked on the top plate of the aluminium box (115). The control, through electrical signal, of the DC motor (140) permits the left-hand and right-hand movement on X axis of the glass slide holder (35) and of the slide coverslip (15) inserted in it, always maintaining the correct optical coupling (FIG. 1B).

The second block of movement (145, 155) is composed of one Y axis linear stage (155), coupled in axis, by means of axle box, with a second DC motor (145). The Y axis linear stage (155) and the DC motor (145) are both locked on the base plate (235). The second block of movement (145, 155) allows the movement on Y axis of the glass slide holder (35) and of the overall components belonging to and locked to the aluminum box (115), internally (60, 65, 70, 75, 80, 85, 90, 95) and externally (140, 150, 165). The control, through electrical signal, of the DC motor (145) permits upward and downward movement on Y axis of the glass slide holder (35) and of the slide coverslip (15) inserted in it, always maintaining the correct optical coupling (FIG. 1B). In summary, the mechanical module of XY movement (FIG. 4) offers the ability to move a glass coverslip in 4 directions (right, left, up, down) through the management of electrical signals piloted by the first electronic board (215). The relative commands are sent by the touch screen interface (270).

The microscope module (FIG. 5) is located under the slide coverslip with the optical axis of the air lens-objective (40) in line with the LED module (FIG. 3) and perpendicular to the glass coverslip (15). The microscope module (FIG. 5) is composed of one air lens-objective (40), one objective holder (160) integrated with one Z axis linear stage (275), one step motor (280), one mirror (180) within its holder (170) locked to the rear vertical plate (240), another mirror (185) within its holder (175) locked to the base plate (235), one filter wheel (190) connected to the rotational axis of one step motor (195) and one CCD camera (200). The microscope module (FIG. 5) is fixed in X and Y axis and the only degree of freedom in which is able to operate is the Z axis. In fact, depending on the type of air lens-objective adopted (40) and on its working distance, some kind of adjustment is required. Therefore it's possible to set the right focus and keeping it during the XY scan of the sample under observation. Due to the high sensitivity of the focus of the image for lens-objectives equal to or greater than 40×, the construction of a stable miniaturized optical device able to properly perform image scanning at high magnification—even 60×—requires a high degree of mechanical precision using 0.01 mm precision aluminum plates (235, 240, 245, 250, 260, 265).

The microscope module contains a lodge for the air lens-objective, thus permitting its interchange. With a focal length of 160 mm, magnifications and numerical aperture of 10× NA=0.25, 20× NA=0.40, 40× NA=0.65 and 60× NA=0.85, it is possible to offer different field of views, ranging from 0.56×0.40 mm with a 10× air lens-objective to 0.087×0.067 mm with a 60× one. The end user could then pre-set the optical device according to his particular requirements, with a pixel size ranging from 400 to 67 nanometers.

The air lens-objectives have different working distance that can be regulated by adjusting the height of the objective holder (160), which is integral with the Z axis linear stage (275). This makes possible the replacement enhancing the range of possibilities of the optical device.

The parallel light beam (outing) exiting from the lens-objective must be at least 160 mm in length, starting from the back focal plane of the lens-objective and ending to a CCD camera. Working on the three geometric spatial dimensions, this distance can be limited by the use of mirrors (180, 185), thus reducing the size of the optical device.

The Z axis linear stage (275), which is locked to the rear vertical plate (240), is provided with a knob handler for manually moving the objective along the Z axis in order to reach the focus on the surface of the slide coverslip (15). The handler is also locked to a step motor (280) coupled, by means of axle box, with the rotational axis of the Z axis linear stage (275). This allows tier the electronic control, with precise automated micro steps, of the Z axis movement.

The control on the Z axis of the focus of the image is quite critical for the detection of sub-diffractive nanoparticles (55), because the evanescent wave (50) diffuses inside the liquid solution only for few hundreds of nanometers. Therefore it is necessary that the air lens-objective (40) stays at a precise height along the Z axis. This can be partially achieved in transmission mode by reaching the focus on the solid-liquid interface, then, in internal reflection mode, operating with a finer tuning by using micro steps.

The step motor (285) is piloted through electrical signals programmed on the first electronic board (215). The related commands are sent by the touch screen interface (270). In front of the CCD camera (200) there is an integrated filter wheel (190), controlled from one step motor (195), where it is possible to insert optical band pass filters, according to the end user requirements in terms of optical detection at certain wavelengths of interest. The proper choice of filter mainly depends on the optical properties in absorption and emission of the nanoparticles (55). The image, either filtered or not, is captured by the CCD camera (200) and finally sent to PC via USB for processing.

The opto-mechanical unit (FIG. 6) briefly summarizes the role of the modules necessary only for laser imaging and is constituted by three modules: the laser module (FIG. 2), the mechanical module for XY handling (FIG. 4) and the microscope module (FIG. 5).

The opto-mechanical unit (FIG. 6) is able to move respectively on X axis the glass slide holder (35) and on Y axis the aluminum box (115), that means the class slide holder (35) plus all the components integrated in and on it (60, 65, 70, 75, 80, 85, 90, 95, 140, 150, 165). The opto-mechanical unit (FIG. 6), structured in this way, is able to provide and conserve the right optical coupling (FIG. 1B) configuration during the process of XY scan of the slide coverslip (15).

The electronic module (FIG. 7) consists of two electronic boards (215, 220) directly interconnected and, both equipped with a microprocessor. A 12V battery can provide enough power to the optical device (FIG. 9). The first electronic board (215) has a USB port (205) for programming of the electrical signals and is supplied through a 12V/2A power supplying plug (210). The first electronic board (215) is equipped with a programmable microcontroller interfaced with the DC motors (140, 145) and the touch screen interface (270). The second electronic board (220), directly connected to the first electronic board (215), is equipped with a programmable microcontroller interfaced to the step motor (195, 280) and the light sources (60, 100). Each electrical signal is controlled through GPIO interface port, by pairs of cables on one side soldered at the positive and negative poles of each single component, and on the other side connected to pins on the first electronic card (215). A dedicated firmware implements all the commands and controls received through the touch screen interface (270). The touchscreen interface (270) of the optical device (FIG. 9) is programmed in order to control the left-hand, right-hand, upward and downward movements of the glass coverslip (15), the step filter wheel (190), the upward and downward movements for the Z axis, the switch on/off of the light sources (60, 100) and their intensities are controlled using pulse width modulation, so the intensity of the light beams coming from the LED and laser modules can be optimized, during observation of a sample, searching the best signal to noise ratio conditions.

Finally, the opto-electro-mechanical unit (FIG. 8) summarizes the combination of the opto-mechanical unit (FIG. 6), the electronic module (FIG. 7) and the LED module (FIG. 3) in a single embodiment. The opto-electro-mechanical unit (FIG. 8) is enclosed in two volumetric units: a parallelepiped box, having maximum dimensions of width× length×height respectively equal to 20×22×13 cm, constituted by aluminium plates (235, 240, 245, 250, 260, 265) and a cylindrical container, having maximum dimensions in diameter×height respectively equal to 7×10 cm. The total volume of the optical device (FIG. 9) is less than 6.5 dm$^3$ and regroups, in this small dimensions, all the basic functionalities of an automated laser microscope.

The opto-electro-mechanical unit (FIG. 8) has components fixed on two aluminium plates, the base plate (235) and the rear vertical plate (240). On the base plate (235) are fixed the second block for linear movement in the Y axis (145, 155), the mirror holder (175) with the mirror (185) integrated to it, the CCD camera (200) with the step motor (195) and the filter wheel (190), and all the electronic boards (215, 220, 225) needed for the control of motors and light sources.

On the rear vertical plate (240) are fixed the Z axis linear stage (275), the step motor (280), the mirror holder (170) with the mirror (180) integrated to it, and the support (230) for the LED module. A precise adjustment of the plates (235, 240) at exactly 90 degrees allows the obtainment of an optical device (FIG. 9) that keeps focus with precision during XY scan process. This makes the optical device suitable for capture giant patchworks of micrometric images upcoming from nanoparticles samples, ad example centrifuged on glass surfaces or printed on microarrays.

The optical device (FIG. 9) contains internally the opto-electro-mechanical unit (FIG. 8) able to perform a scan of a slide coverslip (15) moving within an XY area of 13×13 mm. In particular, the opto-electro-mechanical unit (FIG. 8) is able, in theory, to do a scan also in absence of gravity or in presence of a different gravity even with an air lens-objective at 60× since any component of the optical device (FIG. 9) is fixed in the space and integral to the slide coverslip.

The optical device (FIG. 9) has an external body made of corrected aluminum, obtained by using six aluminium plates (235, 240, 245, 250, 260, 265): the upper plate (260), the glass slide holder (35) and the base plate (235) must be perfectly parallel with a mechanical precision of 0.01 mm. This precision contributes to keep the focus of the image during the scanning process on X and Y axis. In particular, this is mainly achieved by machines able to smooth properly the surface of the aluminium upper plate (260) with precision of 0.01 mm. The front vertical plate (265) is designed to accommodate the touch screen interface (270) and is pointed towards the user for control of commands.

The front vertical plate (265) has a couple of service holes (255) that allows a user to calibrate they device by adjusting the direction of the laser beam (10) exiting from the fissure (95) with the proper angle, so the beam hits the rim of the slide coverslip (15).

The optical device (FIG. 9) can be connected via USB cable, but also via wi-fi, to a desktop computer, or a laptop, or a netbook, or a tablet, and allows, through the installation of a driver, the display of images on the computer monitor using a program for the acquisition of the image, in a similar manner to a plug-and-play webcam.

The quality of the USB port will determine the speed of transmission data and the resolution capacities for the image or video acquisition.

The optical device (FIG. 9) is suitable for detecting and counting, by means of image analysis, both organic materials such as bacteria or human cells, both inorganic materials such as nanoparticles of various elements, as well as the interactions between organic and inorganic matter in liquid solution.

The optical device (FIG. 9) has also been designed and developed to provide images and videos to external general purpose and/or specialized software applications which could be pervasive in several industrial sectors, aiming at improving the quality of the processes in the area of bio-sensing, diagnostics, environmental protection, counterfeiting and biological threat prevention.

Figure 1A:
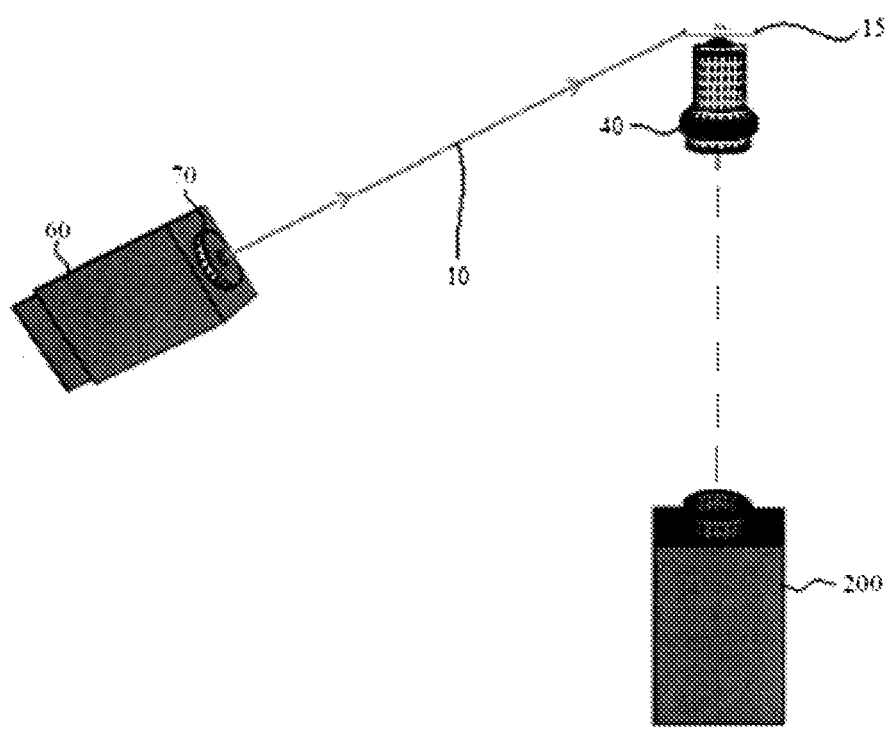
FIG. 1A Optical Coupling Method—High level description and involved elements

This illustration is a high level description of the proposed optical coupling method and the physical element involved with it, namely a laser diode (60) with a lens (70) focusing the light beam (10) on the rim of a glass coverslip (15) at a specific angle of 25±2 degrees, plus an air lens-objective (40) and a CCD camera (200) to observe the sub-diffractive nanoparticles excited from the evanescent wave.

Figure 1B:
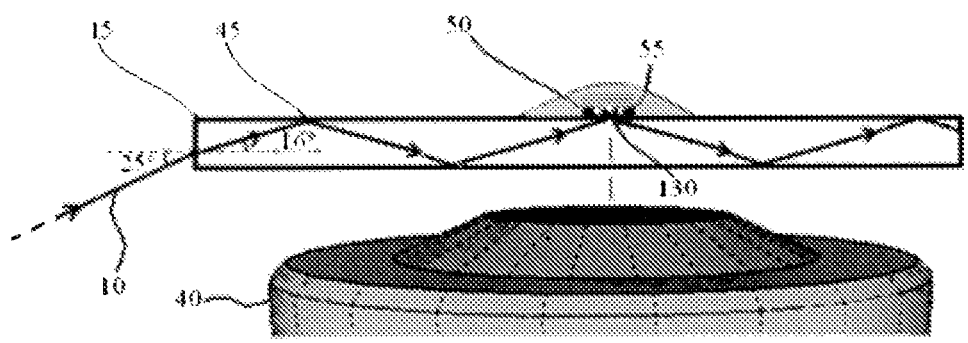

FIG. 1B Optical Coupling Method—Evanescent Wave transmission

This illustration shows, in more detail, how the light beam (10) incident on the rim of a glass coverslip (15) at a specific angle of 25±2 degrees, at the air-glass interface deviates to a 16 degrees angle into the glass coverslip, where internal reflection (45) of the light generates an evanescent wave (50) able to penetrate into the liquid solution where nanoparticles (55) are dispersed.

Figure 2:
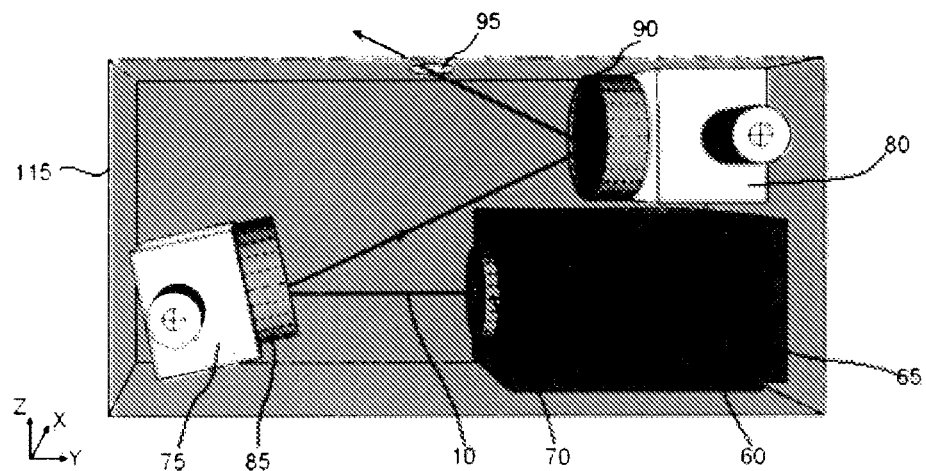

FIG. 2 Laser Module

This illustration shows the laser module, composed of one laser diode (60), one lens (70) and two mirrors (85, 90), jointly assembled to provide a laser beam exiting from the slot (95) located on top of it with an angle of 25±2 degrees.

FIG. 3 Led Module

This illustration shows the internal composition of the LED Module, with the presence of one multicolour RGB chip LED (100), one iris (105) and one condenser lens (110) arranged into a cylindrical container (120) to illuminate the sample under observation in wide-field transmission microscopy.

Figure 4:
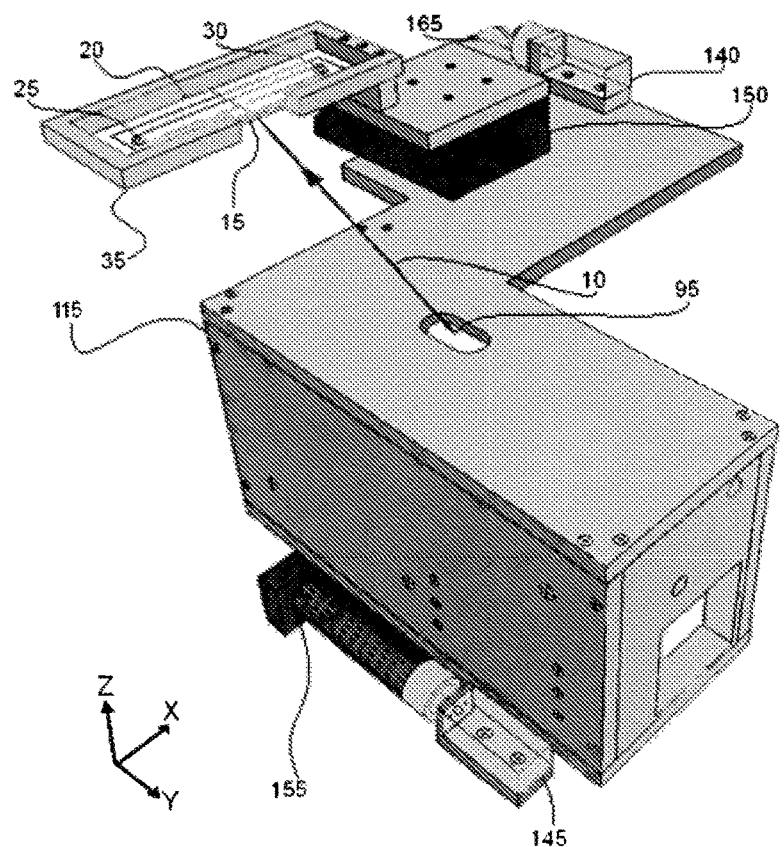

FIG. 4 Mechanical Module for XY handling

This illustration shows the Mechanical Module for XY handling, composed of two blocks of movement: one located on the bottom (145, 155) of the Laser Module and one located on the top of it (140, 150, 165). The two blocks are properly arranged in order to hold the right optical coupling of FIG. 1B during XY scan of a glass coverslip.

Figure 5:
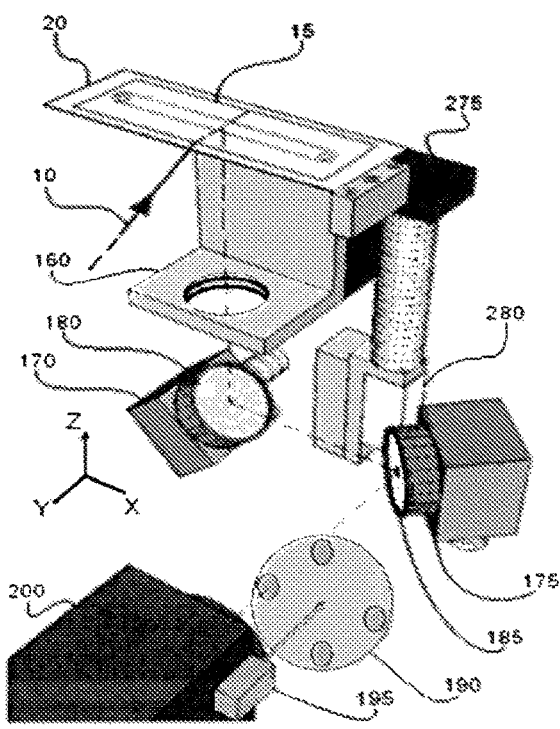

FIG. 5 Microscope Module

This illustration shows the Microscope Module, composed of one lens-objective, here hidden for the sake of clarity, one lens-objective holder (160) integral with the Z axis linear stage (275) and the step motor control (280), two mirrors (180, 185) and one CCD camera (200) with an automated, through another step motor (195), filter wheel (190): Everything is arranged to minimize the necessary optical path in a three dimensional geometry.

Figure 6:
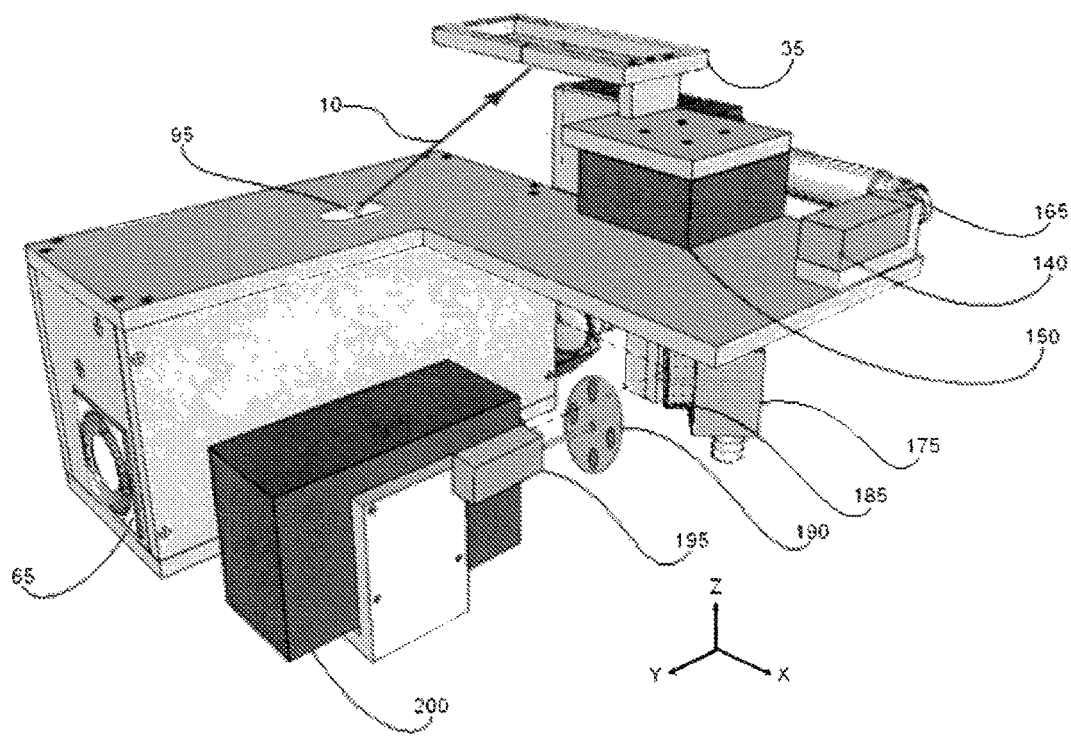

FIG. 6 Opto-Mechanical Unit

This illustration shows the Opto-Mechanical Unit arising from the proper arrangement, in order to minimize the unit overall volume of the Laser Module (FIG. 2), the Mechanical Module (FIG. 4) and the Microscope Module (FIG. 5).

Figure 7:
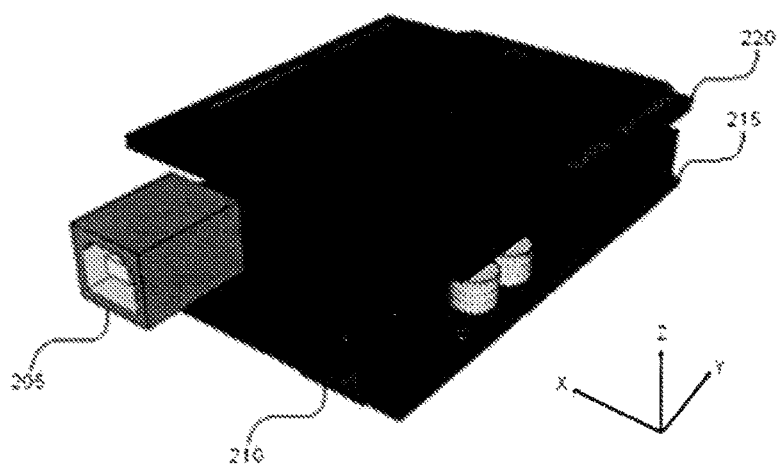

FIG. 7 Electronic Module

This illustration shows the Electronic Module, composed of one electronic board (215) dedicated to 5V signals control and another electronic board (220) dedicated to 12V signals control. The two electronic boards are directly interconnected and can be programmed via a USB port (205). External power supplying, if and when required, is provided via one 12V electric plug (210).

Figure 8:
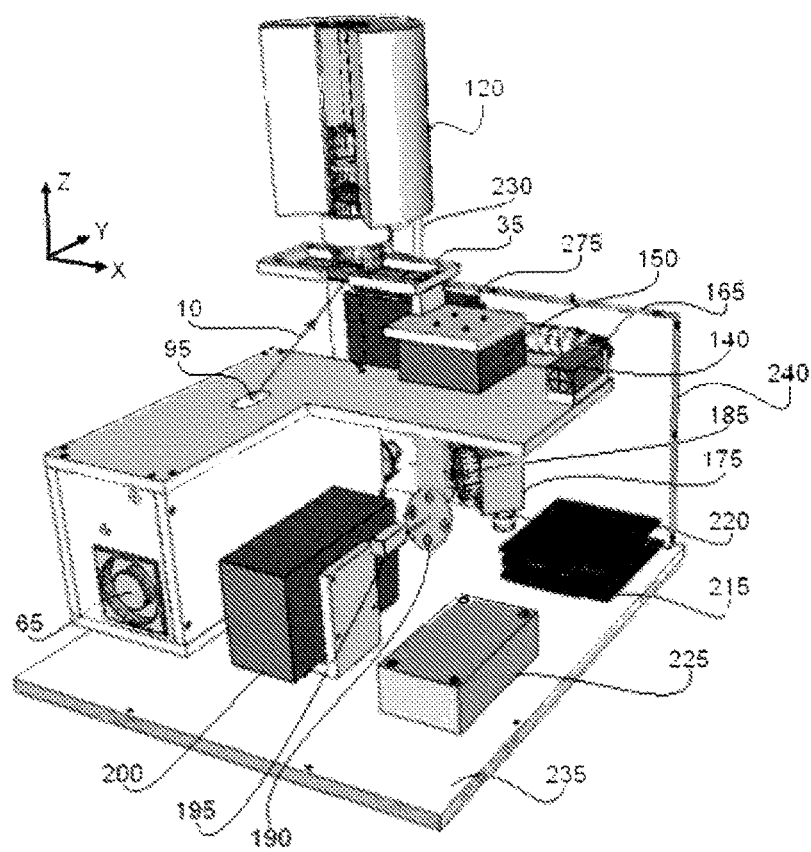

FIG. 8 Opto-electro-mechanical Unit

Figure 3:
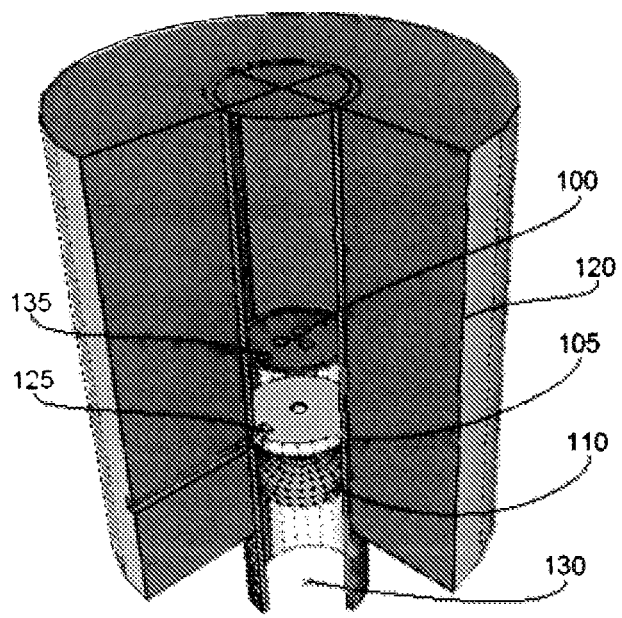

This illustration shows the Opto-electro-mechanical Unit arising from the proper arrangement, in order to minimize the unit overall volume, of the Laser Module (FIG. 2), the LED Module (FIG. 3), the Mechanical Module (FIG. 4), the Microscope Module (FIG. 5) and the Electronic Module (FIG. 7).

Figure 9:
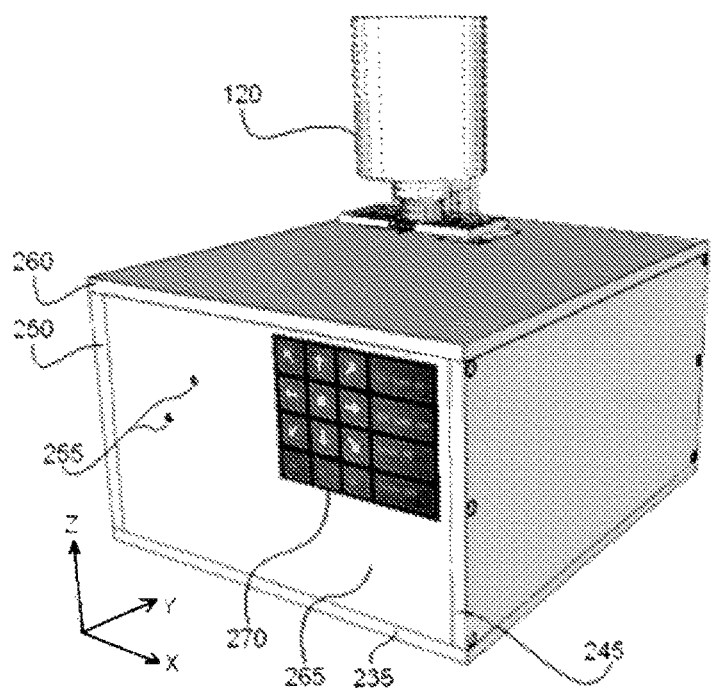

FIG. 9 Optical Device

This illustration shows the optical device having a parallelepiped base with a touch screen in front of it and the LED Module on top of it. The shape of the optical device can protect it from external stray light, thus ensuring the best reliability and sample observation reproducibility thanks to optical isolation.

LIST OF REFERENCES

10—Laser beam
15—Slide coverslip (bare)
20—Glass slide
25—Inlet for the fluid
30—Outlet for the fluid
35—Glass slide holder
40—Air lens-objective
45—Internal reflection
50—Evanescent wave
55—Nanoparticles
60—Laser diode
65—Thermo-electrical cooling
70—Plane-convex lens
75—Mirror holder
80—Mirror holder
85—Mirror
90—Mirror
95—Fissure
100—LED chip multicolour RGB
105—Iris
110—Condenser lens
115—Aluminium box
120—Cylindrical container
125—Square mirror
130—Focal point
135—IR receiver
140—DC motor
145—DC motor
150—X axis linear stage
155—Y axis linear stage
160—Objective holder
165—Couple of gears
170—Mirror holder
175—Mirror holder
180—Mirror
185—Mirror
190—Filter wheel.
195—Step motor
200—CCD camera
205—USB port
210—Electrical plug at 12V
215—First electronic board
220—Second electronic board
225—Electron is board of laser
230—LED module support
235—Base plate
240—Vertical rear plate
245—Right lateral plate
250—Left lateral plate
255—Service holes
260—Upper plate
265—Vertical front plate
270—Touch screen interface
275—Z axis linear stage
280—Step motor
285—Anti-vibration feet

The invention claimed is:

1. An optical device comprising:
a laser module; and
a microscope module,
wherein said laser module is composed of a laser diode emitting a laser beam on a plane-convex lens being focused to hit the rim of a slide coverslip, wherein the rim comprises a thickness of said slide coverslip,
wherein said slide coverslip is on a plane defined as an XY-plane, and said laser beam hits said rim of the slide coverslip with an angle of incidence of 25°+2 with respect to said XY-plane, and
wherein said slide coverslip is a thickness of approximately 0.17 mm, and said microscope module is located perpendicular to said slide coverslip.

2. The optical device according to claim 1, wherein said slide coverslip is glued on a microscope glass slide which is positioned on a glass slide holder.

3. The optical device according to claim 1, wherein said laser beam is directed towards a first mirror attached to a first holder and then towards a second mirror attached to a second holder, said laser diode being closed into a box, said box having a slot though which the laser beam exits with an angle of 25°+2 with respect to the XY-plane.

4. The optical device according to claim 3, further comprising:
a LED module, a mechanical module, and an electronic module;
wherein said LED module is positioned perpendicular to the slide coverslip on a same axis of an air lens-objective;
wherein said mechanical module is configured for XY handling, with a first block of movement provided for X axis, and enabling the movement on the X axis of a glass slide holder with the glass slide inserted therein, and a second block enabling movement on the Y axis of the glass slide holder and all components closed in the box;
and wherein said microscope module is located under said slide coverslip with the optical axis of the air lens-objective in line with the LED module and perpendicular to the slide coverslip.

5. The optical device according to claim 1, wherein the optical device has a maximum size of 6.5 $dm^3$.

6. A method of detection of sub-diffractive nanoparticles, the method comprising:
providing an optical device according to claim 1;
emitting the laser beam to hit the rim of the coverslip with an angle of incidence of 25°+2 with respect to the XY-plane on which said coverslip is positioned, such that an evanescent wave is generated upon the coverslip, said evanescent wave exciting the nanoparticles located upon the coverslip; and
capturing the optical signal generated by the excited nanoparticles.

7. The method of detection of sub-diffractive nanoparticles according to claim 6, wherein said method is implemented in the absence of gravity.

8. The method of detection of sub-diffractive nanoparticles according to claim 6,
wherein a specific optical laser coupling includes one laser diode, one plane-convex lens, one 0.17 mm thick glass coverslip, one air lens-objective and one CCD camera, collectively arranged to detect sub-diffractive spherical nanoparticles until 100 nm in diameter size,
wherein the light source is a laser diode at 405 nm wavelength, emitting at 100 mW of power, configured to generate the laser beam focused on the rim of a bare slide coverslip having 0.17 mm thickness, said bare coverslip being untreated with normal right angle surfaces and without any inclined end face,
wherein said laser beam hits the rim of the coverslip with a round spot of 0.15 mm of diameter and with an angle of incidence of 25±2 degrees, referred to the plane of the slide coverslip and, when the laser beam passes through the air-glass interface, the laser beam changes an incident angle from 25 to 16 degrees, such that an internal reflection is provided and configured to generate an evanescent wave upon the coverslip that is configured to excite the nanoparticles dispersed in liquid transparent solution and located upon the coverslip,
wherein a penetration depth of the evanescent wave field on Z axis is variable between 50 nm up to 700 nm, depending on the refractive index of the liquid solution, either water or glycerin, in which nanoparticles are dispersed,
wherein the optical signal generated from any detected nanoparticle is captured using an air lens-objective and a CCD camera, and a resulting image is captured either in fluorescence or in scattering mode, depending on an insertion of a band-pass filter in front of the CCD camera and detection of nanoparticles occurs on the coverslip at the glass-liquid interface and inside the evanescent wave field generated by internal reflection of the laser beam inside the bare coverslip,
wherein the focal point of the lens-objective is centered at the cross with the line of light driven by internal reflection in the slide coverslip and nanoparticles are deposited on the surface by inserting them into a linear flow channel, obtained between a coverslip and a glass slide, having an inlet and outlet for the liquid solution which contains the nanoparticles, the glass slide and the coverslip being stick together with a silicone film that defines the internal boundaries of the flow channel and the glass slide is then lodged in a glass slide holder integrated into a mobile slide side of a linear stage.

9. The method of detection of sub-diffractive nanoparticles according to claim 8, wherein, in absence of gravity, application of the method does not require the use of oil-based lens objectives and no relevant component of the sub-diffractive nanoparticles detection method can modify its behavior in absence of gravity.

* * * * *